United States Patent
Ott et al.

(10) Patent No.: US 12,116,336 B2
(45) Date of Patent: *Oct. 15, 2024

(54) METHOD FOR THE RECYCLING OR DISPOSAL OF HALOCARBONS

(71) Applicant: GRILLO-WERKE AG, Duisburg (DE)

(72) Inventors: Timo Ott, Duisburg (DE); Christian Diaz-Urrutia, Orleans (CA); Matthias Vogt, Duisburg (DE)

(73) Assignee: LTS LOHMANN THERAPIE-SYSTEME AG (DE)

( * ) Notice: Subject to any disclaimer, the term of this patent is extended or adjusted under 35 U.S.C. 154(b) by 703 days.

This patent is subject to a terminal disclaimer.

(21) Appl. No.: 17/299,764

(22) PCT Filed: Dec. 5, 2019

(86) PCT No.: PCT/EP2019/083798
§ 371 (c)(1),
(2) Date: Jun. 3, 2021

(87) PCT Pub. No.: WO2020/115197
PCT Pub. Date: Jun. 11, 2020

(65) Prior Publication Data
US 2022/0017458 A1 Jan. 20, 2022

(30) Foreign Application Priority Data

Dec. 6, 2018 (EP) .................................... 18210744
May 22, 2019 (EP) .................................... 19176007

(51) Int. Cl.
*C07C 303/06* (2006.01)

(52) U.S. Cl.
CPC ................................. *C07C 303/06* (2013.01)

(58) Field of Classification Search
CPC ...... C07C 303/06; C07C 309/06; Y02C 20/30
See application file for complete search history.

(56) References Cited

U.S. PATENT DOCUMENTS

| 2,698,348 A | 12/1954 | Giraitis |
| 3,557,231 A | 1/1971 | Kurtz et al. |
| 4,649,209 A * | 3/1987 | Geering ................. C07C 303/24 558/46 |
| 4,902,493 A | 2/1990 | Walles et al. |
| 5,723,630 A | 3/1998 | Cheburkov et al. |
| 11,634,385 B2 * | 4/2023 | Ott ........................ C07C 303/06 562/118 |

FOREIGN PATENT DOCUMENTS

| CN | 1286273 A | 3/2001 |
| CN | 101195592 A | 6/2008 |
| CN | 104725283 B | 9/2016 |
| FR | 660023 A | 7/1929 |
| GB | 892148 A | 3/1962 |
| JP | 2001512455 A | 8/2001 |
| WO | 2008141179 A1 | 11/2008 |
| WO | WO2008/141179 * | 11/2008 |
| WO | 2020115197 A1 | 6/2020 |

OTHER PUBLICATIONS

Mukhopadhyay et al. (Synthesis of Trifluoromethanesulfonic Acid from CHF3, Organic Process Research & Development, 8, 660-662, Published 2004) (Year: 2004).*
Japanese Office Action dated Aug. 23, 2023 in connection with Application Serial No. 2021530095.
Patent Cooperation Treaty, "International Search Report and Written Opinion for PCT Patent Application No. PCT/EP2019/083798", Mailed Date: Mar. 27, 2020, 16 pages.
Banks, et al., "Per- and Poly-Fluorinated Aliphatic Derivatives of the Main-Group Elements", In Royal Society of Chemistry, vol. 3, Jan. 1, 1976, pp. 304-305.
Chinese Office Action dated Feb. 2, 2023 in connection with Application Serial No. 201980076466.0.
Chinese Office Action dated Aug. 31, 2023 in connection with Application Serial No. 2019800764660.

* cited by examiner

*Primary Examiner* — Yevgeny Valenrod
*Assistant Examiner* — Blaine G Doletski
(74) *Attorney, Agent, or Firm* — Eschweiler & Potashnik,

(57) ABSTRACT

The present invention relates to a method for recycling and/or disposal of halocarbons, particularly fluorinated alkanes, such as trifluoromethane, by reacting said halocarbons with sulfur trioxide, particularly to form halide sulfonic acids and sulfur dioxide.

20 Claims, No Drawings

METHOD FOR THE RECYCLING OR DISPOSAL OF HALOCARBONS

CROSS-REFERENCE TO RELATED APPLICATIONS

This application is a national stage entry of PCT/EP2019/080685, published as WO/2019/083798, filed on Dec. 5, 2019, which in turn, claimed priority to EPO application number 18210744.1, filed on Dec. 6, 2018 and to EPO application number 19176007.3, filed on May 22, 2019. These prior applications are incorporated herein by reference.

The present invention relates to a method for recycling and/or disposal of halocarbons, particularly fluorinated alkanes, such as trifluoromethane, by reacting said halocarbons with sulfur trioxide, particularly to form hydrogen halides, carbon dioxide and sulfur dioxide. Recycling/disposal within the meaning of the present application means the conversion of halocarbons to useful substances.

Halocarbons are hydrocarbons in which at least one H-atom is replaced by a halogen. The hydrocarbon can be any hydrocarbon, i.e. an alkane, an alkene, an alkine, it can be linear, branched or cyclic, substituted or un-substituted. Haloalkanes which are part of the halocarbons, also known as halogenalkanes or alkyl halides, are a group of chemical compounds structurally derived from alkanes by replacing one or more hydrogen atoms by halogen atoms. They are widely used as flame retardants, fire extinguishants, refrigerants, propellants, solvents and pharmaceuticals.

The international ban of hydrochlorofluoroalkanes in the last century (Montreal Protocol 1987) due to their ozone depletion power triggered the development of new fluoroalkanes as an alternative for refrigerants and gas propeller, among other applications. The unique properties of fluoroalkanes, such as high stability and inertness, are ideal for the replacement of hydrochlorofluorocarbons. Later discoveries, however, have shown that fluoroalkanes are potent greenhouse gases. For example, the small fluoroform ($CF_3H$) has a global warming potential equivalent to 14,800 molecules of $CO_2$.

International efforts successfully achieved the gradual prohibition of fluoroalkanes and their intended reduction by 85% compared to their baselines until 2045 (Kigali Amendments 2016 to the Montreal Protocol). Alternatives gases with a lower global warming potential, which are also harmless to the ozone layer, are currently under investigation and many successful products are already in the market.

However, several large-scale industrial processes generate fluoroalkanes as a by-product. For example, the synthesis of chlorodifluoromethane ($HCF_2Cl$); which is used as a refrigerant, a blend component for foam materials and a chemical precursor of polytetrafluoroethylene (Teflon); produces large amounts of $CF_3H$ with the additional costs for storage or recycling in order to comply with the current regulations. Storage of fluoroalkanes is economically not viable and recycling appears to be the only reasonable alternative.

Current methods (A. McCulloch, Incineration of HFC-23 waste streams for abatement of emissions from HFCFC-22 production: A review of scientific, technical and economic aspects, University of Bristol, 2005) are based on the thermo-catalytic decomposition of fluoroalkanes using $H_2$ and $CO_2$ between 300 to 900° C., affording CO and HF. High temperatures and HF manipulation arise as the main constraints for widespread application of these methods. New methodologies are needed for the recycling of halocarbons, particularly fluoroalkanes, derived from industrial scale manufacturing.

It is thus the object of the present invention to provide a new method for the recycling or disposal of halocarbons, particularly fluoroalkanes, and their conversion to substances, which are neither harmful to the ozone layer nor show a considerable global warming potential. Particularly, it is the object of the invention to provide an efficient method for converting halocarbons to useful substances.

Surprisingly it was found that halocarbons can react with $SO_3$ leading to the formation of a sulfonic acid of the halogen of the halocarbon. In a first embodiment, the object of the present invention is therefore solved by a method for the conversion of halocarbons, wherein a halocarbon is reacted with $SO_3$, preferably the halocarbon is reacted with oleum. Oleum is fuming sulfuric acid. It refers to solutions of $SO_3$ solved in $H_2SO_4$. If stored, $SO_3$ reacts with $H_2SO_4$ leading to the formation of disulfuric acid. If used as a component of a reaction, the disulfuric acid usually dissociates into $SO_3$ and $H_2SO_4$ again, so that $SO_3$ is usually the reaction partner in the reaction.

Halocarbons within the meaning of the present invention are hydrocarbons in which at least one H-atom is replaced by a halogen. The hydrocarbon can be any hydrocarbon, i.e. an alkane, an alkene, an alkine, it can be linear, branched or cyclic, substituted or un-substituted. Also within the scope of the present invention is if the hydrocarbon is an aryl compound, such as phenol, naphthol, benzol etc. Substituted within this context is to be understood in that a H-atom or a C or CH group or a $CH_2$ group or a $CH_3$ group within the halocarbon is replace by a substituent. Such a substituent may be —COOH, C(O), N, P, S, O, C(O)O, wherein free valences are saturated with hydrogen, if necessary.

If in the following it is mentioned that halocarbons react with $SO_3$, it is to be understood that it is the reaction either with pure $SO_3$ or with oleum. Preferably oleum is present to enable the reaction between the halocarbon and $SO_3$. It is also within the scope of the present invention that sulfuric acid or water is provided in a first step and $SO_3$ is added afterwards so that oleum forms in situ in the reaction mixture. Of course, it is also possible to first provide $SO_3$ and add water or sulfuric acid afterwards, leading again to the formation of oleum.

$SO_3$ can be solved in $H_2SO_4$ in a large range of concentrations. Thus, within the meaning of the present application oleum comprises 1% to 100% by weight of $SO_3$, preferred the amount of $SO_3$ in the oleum is within a range of from 10% to 95%, especially from 15% to 90%, preferably from 20% to 88%, preferred from 25% to 85% or from 30% to 80%, especially preferred from 35% to 75% or from 40% to 70%. Preferably, the amount of $SO_3$ is 65% by weight or less, especially 60% by weight or less. The higher the amount of $SO_3$, the higher the risk in handling oleum and to control the reaction conditions, under which a safe reaction between the halocarbon and the oleum takes place. If the concentration of $SO_3$ is low, especially below 10%, the reaction time is quite long. Therefore, effective reactions can take place especially at $SO_3$ concentrations in oleum of 25% to 70% by weight, preferably 30% to 65% by weight.

If in the present application amounts are mentioned in %, it always refers to % by weight if not explicitly mentioned different.

Particularly a halocarbon is reacted with sulfur trioxide to form the corresponding sulfonic acid. The corresponding sulfonic acid in this context refers to any sulfonic acid comprising the same halogen element (F, Cl, Br, I, As) as the employed halocarbon. In a case, where the halocarbon comprises more than one type of halogen (F, Cl, Br, I, As), multiple types of sulfonic acids are formed.

For example, if $HCF_3$ reacts with oleum, the reaction products are $FSO_3H$, $SO_2$ and $CO_2$. $SO_2$ has a high solubility in oleum. It can be re-oxidized to $SO_3$ and subsequently used in further halocarbon recycling. $FSO_3H$ can be used as industrial chemical and $CO_2$ has a significantly smaller global warming potential than the converted halocarbons.

Alternatively, if $H_2CF_2$ reacts with oleum, $FSO_3H$ is formed:

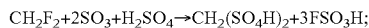

The $CH_2F_2$ reaction with oleum results in the formation of fluorosulfonic acid and methylene di(sulfate) (MDS). The reaction proceeds, in contrast to the similar reaction utilizing $CHF_3$, without oxidation of the carbon. Hence, the formation of $CO_2$ and, respectively, $SO_2$ is not observed.

MDS is basically a derivative of formaldehyde: Upon hydrolysis formaldehyde and sulfuric acid is released. MDS finds relevance as biocide, slow-release antimildew agent for artificial board, in antibacterial and antiseptic multi-function aldehyde-free stalk artificial board, as electrolyte in battery applications in its condensed dimerized form.

Without being bound to theory, the following reaction may generally take place (with X being a halogen):

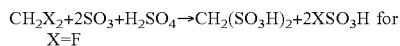

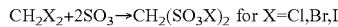

Reaction of with excess $CH_2X_2$:

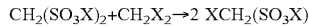

The following hydrolysis may take place under the respective reaction conditions:

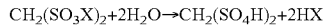

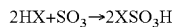

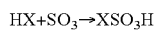

In the following, the assumed reaction is depicted:

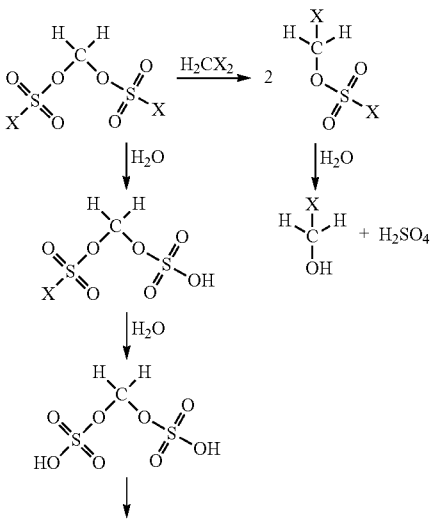

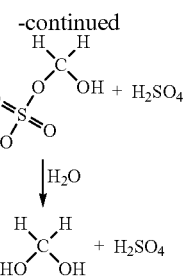

But not only alkanes with only one C-atom can be converted into the corresponding sulfonic acid, but also alkanes with higher C-number. The halocarbon, which can be converted with oleum, needs at least one structural element where a nucleophilic, electrophilic or radical attack is possible. This may be for example a double or a triple bond or a C—H, C—Cl, —C—Br, Cl, C—COOH, C—SO$_2$H, or C—SO$_3$H, C—NH$_2$, C—OH, C=O, CN-group for example.

It is preferred that in cases where the halocarbon comprises two, three, four or more C-atoms, that the reaction mixture contains not only the halocarbon and oleum but also an oxidant. Said oxidant should be added stoichiometric compared to the amount of halocarbon being present in the reaction mixture. Suitable oxidants are for example peroxides, $H_2O_2$, $K_2S_2O_8$ and other stable compounds. They will be discussed in more detail below.

A halocarbon which may be recycled/converted with a method according to the present invention is for example $F_3C$—$CHF$=$CH_2$ (1234yf), which is a cooling medium for air conditions, especially for air conditions in cars and other vehicles. Again, reacting said compound with oleum and an oxidant results in the formation of $SO_2$ and $FSO_3H$. Further, long chain halocarbons, such as halogenated surfactants with —COOH or —SO$_3$H terminal groups can be converted into $XSO_3H$ (X being the halogen) and $SO_2$ with the addition of oleum. Not only linear but also cyclic halocarbons can be converted with the process of the present invention.

The inventive method provides a simple and cheap method for the recycling or disposal of halocarbons as well as their conversion into useful materials, particularly of halocarbons produced as side products in industrial processes, such as the production of Teflon. The method can be carried out in small facilities directly at the site, where the halocarbons are produced.

The inventive conversion of halocarbons with sulfur trioxide takes place without the need for any metal catalysts. Preferably, the inventive method is performed in the absence of metal catalysts.

The inventive method may be carried out using peroxides formed in situ or diluted peroxide salts such as $K_2S_2O_8$ as catalysts or in stoichiometric amount. In principle, any peroxide stable at room temperature may be employed as catalyst. Particularly, peroxoacids of oxoacids or salts thereof may be employed. More specifically, peroxoacids of oxoacids of sulfur or salts thereof may be employed. Alternatively, a mixture of hydrogen peroxide and an oxoacid may be employed. Specific examples comprise $H_2S_2O_8$, $K_2S_2O_8$, $NaS_2O_8$, $H_2SO_5$, $KHSO_5$, $NaHSO_5$ and the like. These catalysts/oxidants enable the reoxidization of $SO_2$ to $SO_3$. Thus, the amount of $SO_3$ needed is reduced. This effect is especially relevant if the halocarbon comprises only one C-atom.

The stoichiometric addition of an oxidant seems to be necessary if the number of C-atoms in the halocarbon is >1, i.e. 2, 3, 4, 5, 6, 7, 8, 9, 10 or more. Here, the oxidizing agent activates the halocarbon towards degradation. With the help of an oxidation catalyst/oxidating agent/oxidant, the reaction is getting more reactive. Without being bound to theory, it is assumed that the oxidation catalyst/agent, especially a peroxide compound, helps in oxidizing the alkyl chain towards $CO_2$. Oxidation catalyst and oxidating agent or oxidant are used for the same compounds. The catalyst is added in catalytic amounts, which is less than stoichiometric, whereas the peroxide compound is added stoichiometric if it is used as oxidating agent or oxidant. Oxidating agent and oxidant are used as synonyms in the present application.

The halocarbons may be pressurized to their vapour pressure or may be used as a liquid if the compound is liquid at room temperature.

Preferably, sulfur trioxide is employed in an excess with respect to the halocarbon. The molar ratio between halocarbon and sulfur trioxide is preferably in the range of from 1:100 to 1:1, more preferably from 1:25 to 1:1, particularly from 1:5 to 1:3.

In a preferred embodiment, the halocarbon is reacted with sulfur trioxide at a temperature in a range of from 0° C. to 200° C. Preferably, the temperature is in the range of from 20° C. to 180° C., especially from 50° C. to 160° C., preferred from 60° C. to 150° C., more preferably from 80° C. to 125° C., for example from 100° C. to 120° C. The higher the reaction temperature, the faster and more effective the reaction. But too high temperature also results in extremely aggressive reactions conditions and thus a reactor has to be used being stable under these conditions. At a temperature range between 80° C. and 130° C., the reaction is effective and reactors with standard components can be used, resulting in an economic process. Additionally, at higher temperatures, the solubility of $SO_2$ in $H_2SO_4$ is getting worse. As the reaction is in an equilibrium, the reaction is improved if the products are removed. Higher oleum concentrations allowing for higher $SO_2$ tolerance and thus increased yields. Due to the solvation process of $SO_2$ in $H_2SO_4$, $SO_2$ is quasi removed, resulting in an increase in effectivity of the reaction. Removal of $SO_2$ and $CO_2$, if formed, is also possible with an absorber comprising 20 wt. % NaOH solution, for example.

In a preferred embodiment, the halocarbon is reacted with sulfur trioxide at a pressure of 1 to 200 bar. Preferably, the pressure is in the range of from 10 to 100 bar, particularly 25 to 40 bar.

The halocarbon may comprise any halogen. Preferably, the halocarbon is a fluorinated, chlorinated and/or brominated derivative of an alkane, or alkene, or alkine. The halocarbon may comprise a single or multiple halogen atoms. The halogen atoms may be all of the same halogen element, that means all halogen atoms may be either fluorine, chlorine or bromine atoms. Alternatively, the halocarbon may comprise more than one type of halogen, for example, both fluorine and chlorine, both fluorine and bromine, both chlorine and bromine, or fluorine, chlorine and bromine.

The halocarbon comprises at least one halogen atom bonded to a carbon atom. The halocarbon may comprise one or more carbon atoms bonded to one or more halogen atoms. The halocarbon may be generally disclosed as $C_nH_{(2n+2)-m}X_m$. In a more general way, it may be disclosed as R—$X_m$, with R being -alkyl, -alkenyl, -aryl, and X being F, Cl, or Br, preferably X is F. The number of Halogen-atoms is only limited to the number of available bonds, i.e. if all H-atoms of a compound are replaced, X corresponds to the number of H-Atoms in R. At least, m=1.

The halocarbon is a halogenated derivative of an alkane, or alkene, or alkine. Said alkane, or alkene, or alkine is preferably a branched or unbranched alkane or alkene, or alkine with a carbon number in the range of from 1 to 20, especially 1 to 15, preferably 1 to 10, particularly 1 to 5. This is to be understood, that all numbers in between this range are disclosed as well. If the carbon number is for example from 1 to 20, it has the meaning of 1 or 2 or 3 or 4 or 5 or 6 or 7 or 8 or 9 or 10 or 11 or 12 or 13 or 14 or 15 or 16 or 17 or 18 or 19 or 20. This is analogue for the preferred ranges.

In a preferred embodiment said alkane may be methane, ethane, propane, butane, isopropane or isobutane.

Preferably, the halocarbon is $HCF_3$, $F_3C$—$CHF$=$CH_2$, Lindane, halogenated surfactants or halogenated sulfonic surfactants, 1,1,1,2 tetrafluorethane (R134), PFOAs (perfluoro octanoic acids), $CH_2F_2$, $CH_3F$, $CF_4$, all environmentally harmful refrigerants containing F and/or Cl, refrigerants containing F and/or Cl.

In a preferred embodiment, the reaction mixture may comprise a co-catalyst M-R, wherein M is a metal, preferable a transition metal, particularly a first row transition metal, with an oxidation state of +1 to +7, and R is —H, —OH, —$CH_3$, —O—$CH_3$, —F, —Cl, —Br, —$C_2H_5$ or a higher alkane, —$OC_2H_5$ or a higher oxyalkane, or a suitable inorganic counter anion. Particularly metal salts such as CuCl, $NiSO_4$, $CoCl_2$, $MnCl_2$ or $VCl_2$ are preferred.

In a particularly preferred embodiment of the invention, the halocarbon is a fluorinated alkane. In this embodiment, the object of the present invention is solved by the decomposition of fluoroalkanes to $HSO_3F$, $CO_2$ and $SO_2$, in fuming sulfuric acid.

In a preferred embodiment, the flouroalkane comprises at least one compound of formula (I):

$$RF_x \quad \quad (I)$$

wherein R is a branched or unbranched alkyl group, especially a methyl, ethyl, propyl, butyl, isopropyl, isobutyl group, or a higher alkyl group, wherein the alkyl group may optionally be halogenated with one or more fluorine atoms on any position at the secondary or tertiary carbon. X is the number of Fluorine atoms which in maximum is the number of atoms needed to obtain a saturated Fluoro-carbon-molecule.

The fluoroalkanes may be pressurized to their vapour pressure or used as a liquid, in case of the compound is a liquid at room temperature. The decomposition of the fluoroalkanes is depicted in the following reaction

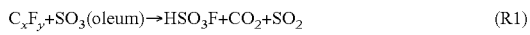

$$C_xF_y + SO_3(\text{oleum}) \rightarrow HSO_3F + CO_2 + SO_2 \quad \quad (R1)$$

wherein x and y are the same or different integers in the range of from 1 to 20.

Fluorosulfuric acid, $HSO_3F$, is considered a mixture of anhydride of sulfuric acid and hydrogen fluoride and hence a precursor of HF. Applications of $HSO_3F$ include as catalyst for alkylation, isomerization, cycloaddition, ring-opening polymerization and fluorosulfonation, among other examples. The $SO_2$ can be easily recycled to $SO_3$, and the $CO_2$ generated does not represent a global warming potential as high as compared to fluoroalkanes (e.g., 14,800 for $CF_3H$ vs 1 for $CO_2$).

The separation of $HSO_3F$ can be done using its wide liquid range (melting point=−89.0° C., boiling point=162.7° C.) and the relative low boiling point of $SO_3$ (boiling point=45° C.), to easily obtain highly concentrated solutions of $HSO_3F$ in sulfuric acid. The unused $SO_3$ can be recycled again for a second batch. This strategy provides a simple and safer alternative to breaking down fluoroalkanes into simple molecules. The formation of fluoro sulfuric acid $HSO_3F$ prevents the release of corrosive and highly toxic HF into the reactor allowing for the use of conventional materials for the reactor (e.g., stainless steel).

In a preferred embodiment, the product mixture after the decomposition of the halocarbon, particularly fluoroalkanes, can be separated by distilling off $SO_2$ (recycling it back to $H_2SO_4$) and $SO_3$. Optionally, $FSO_3H$ can be used such as it is in the mixture with fuming sulfuric acid.

$SO_2$ and $CO_2$ can be absorbed into NaOH solutions and separated.

Methylen bis(chlorosulfate) (MBCS) $(CH_2(SO_3C_1)_2)$, Chloromethyl chlorosulfate (CMCS) $(ClCH_2(SO_3C_1))$ can be extracted from the reaction mixture in $CH_2Cl_2$. Evaporation of the volatile $CH_2Cl_2$ gives rise to the pure products.

Methylen bis(halosulfate) MBXS $(CH_2(SO_3CX)_2)$, Halomethyl halosulfate (XMXS) $(XCH_2(SO_3X))$ X=halogen F; Cl, Br, I components may be extracted from the reaction mixture in a suitable organic solvent (e.g. $CH_2Cl_2$, $CHCl_3$, hexafluorobenzene, per-fluorinated solvents, partially fluorinated solvents).

The device for the recycling process of halocarbons, particularly fluoroalkanes, may comprise a stainless-steel reactor where the halocarbons, particularly fluoroalkanes, are added as liquid or gas depending on the specific vapour pressure of each reagent. Since HF is potentially generated in this process and trapped as $HSO_3F$, there is no need for the use of special materials. If the halocarbons, particularly fluoroalkanes, are gases, the reactor needs to be pressurized to an adequate pressure that allows the right solubility in fuming sulfuric acid.

The device to carry out the decomposition of halocarbons can be set up next to the industrial process where the halocarbons and particularly fluoroalkanes are produced, in order to avoid transportation costs. Alternatively, the device might be located in an integrated facility where $SO_3$ is produced and widely available using the existing infrastructure.

In an alternative embodiment, the object of the invention is solved by a process for the decomposition of fluoroalkanes in fuming sulfuric acid comprising the steps of
i) providing fuming sulfuric acid at concentration between 30% to 99%;
ii) reacting the fuming sulfuric acid with a fluoroalkane, especially trifluoromethane, in a high-pressure autoclave or laboratory reactor;
iii) setting a pressure of from 1 to 200 bar;
iv) optionally introducing a peroxide or peroxide salt as define above as catalyst if the halocarbon comprises 1 C-atom, and stoichiometrically if the number of C-atoms in the halocarbon is >1.
v) controlling the temperature of the reaction mixture at 0° C. to 150° C., preferably 55 to 100° C., more preferably 60 to 70° C.;
vi) if necessary purifying the reaction product, for example, by distillation or extraction.

EXAMPLES

Example 1: Procedure for the Decomposition of Fluoroform to Fluorosulfuric Acid

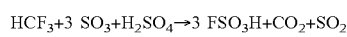

$HCF_3 + 3 SO_3 + H_2SO_4 \rightarrow 3 FSO_3H + CO_2 + SO_2$

In a 4 L stainless steel high-pressure reactor containing 1.789 kg of 36% fuming sulfuric acid was added 285 g fluoroform (4.07 moles). The reactor was sealed and heated to 100° C. and the stirrer speed was set to 350 rpm. After 24 h at constant stirring, the excess pressure is released to a set of scrubbers filled with sulfuric acid and the excess fluoroform, if it is any, was stored in a stainless steel cylinder avoiding the release to the atmosphere. The pressure inside the reactor remains constant at 30.7 bar indicating the existence of dissolved $CF_3H$ in the liquid phase and gaseous $CF_3H$ in the headspace. A liquid sample is transferred to a J-Young NMR tube and $^{19}F$ NMR was measured against an internal standard showing 20% yield of fluorosulfuric acid (based on the initial moles of fluoroform).

Example 2: Procedure for the Decomposition of Fluoroform to Fluorosulfuric Acid a) In a 400 mL stainless steel high-pressure reactor containing 288.2 g of 34% fuming sulfuric acid was added 19 g fluoroform (0.27 mol) increasing the pressure of the reactor to 17.3 bar. The reactor was sealed and heated to 80° C. and the stirrer speed was set to 400 rpm. The initiator was prepared dissolving 2.65 g $K_2S_2O_8$ (9.8 mmol) in 12 mL $H_2SO_4$ (98%), this mixture was added into the reactor using a HPLC pump. After 4 days at constant stirring, the excess pressure was released to a set of scrubbers filled with sulfuric acid and the excess fluoroform was stored in a stainless-steel cylinder to avoid direct release to the atmosphere. A liquid sample was transferred to a J-Young NMR tube and $^{19}F$ NMR was measured against an internal standard showing 57% yield of fluorosulfuric acid (based on initial moles of fluoroform).

b) Preparation without Additional Oxidant OLEUM65:

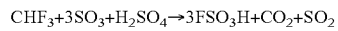

$CHF_3 + 3SO_3 + H_2SO_4 \rightarrow 3FSO_3H + CO_2 + SO_2$

A small stainless steel reactor (450 mL, Parr Instruments) equipped with a glass liner was charged with oleum 65 (292.5 g, 2.37 mol $SO_3$) at 40° C. Under vigorous steering, the sealed vessel was heated to 100° C. and reached a pressure of 4.2 bar. Next the reactor was pressurized with $CHF_3$ to reach an overall pressure of 15.3 bar (94 mmol $CHF_3$). The reaction mixture was stirred (900 rpm) for additional 22 h. After that, the reactor was cooled down to 40° C. and all volatiles were released to scrubbers filled with sulfuric acid. The liquid reaction mixture was recovered and stored in 100 mL glass SCHOTT bottles.

A small sample (ca. 0.7 mL) was transferred to an NMR tube with Teflon cap and subjected to an analysis via $^{19}F\{^1H\}$ NMR spectroscopy The yield of $FSO_3H$ (28.2 g, 282 mmol) was determined via comparison of the relative peak integral to an internal standard ($C_6F_6$) revealing the quantitative conversion of $CHF_3$ into $FSO_3H$.

Example 3: Procedure for the Decomposition of Difluoromethane ($CH_2F_2$)

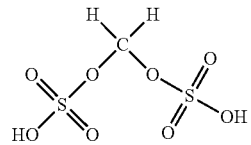

A small stainless-steel reactor (450 mL, Parr Instruments) equipped with a glass liner was pressurized with $CH_2F_2$ at 60° C. to reach an overall pressure of 15.1 bar (0.243 mmol CH$_2$F$_2$); Reaction 1. Subsequently, oleum 35 (307.2 g, equates 1.23 mol SO$_3$) was pumped into the reactor. The temperature was kept at 50° C. and a pressure of 19.2 bar was observed. Upon stirring (900 rpm) the pressure drops to 11.5 bar. Under vigorous steering, the sealed vessel was heated to 60° C. After 30 h the pressure dropped to atmospheric pressure. A small sample for $^{19}$F NMR spectral analysis was taken from the reactor before it was pressurized for a second run with 12.8 bar CH$_2$F$_2$ (0.20 mol) at 60° C. After 36 h the pressure in the reactor reached 1.5 bar; Reaction 2.

The yield of FSO$_3$H in Reaction 1 was (45.1 g, 0.451 mol, Yield with respect to CHF$_3$ 93%) determined comparing the relative peak integral to an internal standard (28.8 mg C$_6$F$_6$). $^{19}$F{$^1$H} (40.89 MHz) NMR s 45.7 (FSO$_3$H); s 161.5 ppm (C$_6$F$_6$) ppm.

The reactor was cooled down to 40° C. and all volatiles were released to scrubbers filled with sulfuric acid. The liquid reaction mixture was recovered and stored in 100 mL glass SCHOTT bottles. A small sample (ca. 0.7 mL) was transferred to an NMR tube with Teflon cap and subjected to an analysis via $^{19}$F{$^1$H} NMR spectroscopy revealing the conversion of CH$_2$F$_2$ into FSO$_3$H and, the organic product methylenedisulfate (MDS, CH$_2$(SO$_4$H)$_2$).

The yield of FSO$_3$H in Reaction 2 (second CHF$_3$ charge) was (28.4 g, 0.284 mol, yield with respect to CHF$_3$ 70%) determined via comparison of the relative peak integral to an internal standard (C$_6$F$_6$).

Example 4: Procedure for the Efficient Decomposition of Dichloromethane (CH$_2$Cl$_2$) without Usage of a Catalyst

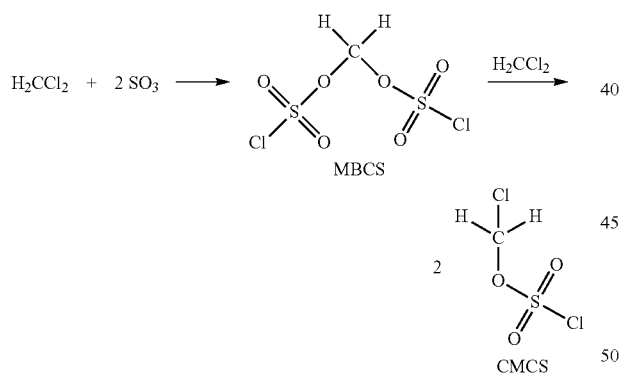

A Fisher Porter pressure reaction vessel equipped with pressure gauge and magnetic stirbar was charged with Oleum 34 (27,277 g). Dichloromethane (DCM, 3 mL) was added slowly directly into the oleum without cooling. Caution, the reaction is violent, when DCM is not carefully added dropwise. The reaction mixture forms two phases. The Fisher Porter vessel was closed and the mixture was heated to 90° C. under vigorous stirring. After 3 h the stirring was stopped and the reaction mixture was allowed to cool down to ambient temperature. At this point, no phase separation was present.

Subsequently, a small sample (ca. 0.7 mL) was transferred to an NMR tube with Teflon cap and subjected to an analysis via $^1$H and $^{13}$C{$^1$H}, and $^{13}$C$^1$H HSQC NMR spectroscopy revealing a full conversion of CH$_2$C$_2$ (s, 5.36 ppm in NMR spectrum) and formation of the major product methylene bis(chlorosulfate) MBCS ($^1$H NMR br s, 6.07 ppm, $^{13}$C{$^1$H}, NMR s 91.77 ppm)

When an excess of CH$_2$Cl$_2$ is present, chloromethyl chlorosulfate (CMCS) is subsequently formed.

NMR chemical shifts (ppm) reported by Bethell et al. Org. Biomol. Chem. 2004, 2, 1554-62. MBCS: $^{13}$C: 92.18 $^1$H: 6.14 in CDCl$_3$ CMCS: $^{13}$C: 77.32 $^1$H: 5.96 in CDCl$_3$ NMR Chemical Shifts (ppm) Found:
MBCS: $^{13}$C: 91.77 $^1$H: 6.07 in H$_2$SO$_4$ CMCS: $^{13}$C: 76.00 $^1$H: 5.86 in H$_2$SO$_4$
Isolation:

MBCS and CMCS can be extracted from the reaction mixture: The reaction mixture was treated carefully with water to quench residual SO$_3$. Subsequently the mixture was extracted three times with dichloromethane (ca 3 mL each extraction). The organic layer was filtered through a PTFE syringe filter and all volatiles where evaporated at atmospheric pressure to obtain the pure products.

Example 5: Preparation of Fluoro Sulfonic Acid (FSO$_3$H) Via the Thermal Decomposition of 1,1,1,2 Tetrafluorethane (R134) in Fuming Sulfuric Acid

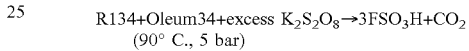
(90° C., 5 bar)

A high pressure NMR tube (NORELL, EXTREME Series Level 3, thin wall, Kalrez O-rings) was charged with 0.5 mL Oleum34 and subsequently pressurized with 5 bar 1,1,1,2 tetrafluorethane (R134)). The reaction was followed by $^1$H and $^{19}$F NMR spectroscopy.
Starting Material:

$^{19}$F (40.89 MHz) NMR of R134 in Oleum34: −75.5 (3F, dt, J=15.9; 8.1 Hz, CF$_3$); −236.4 (1F, tq J=45.5; 15.6, ppm, CH$_2$F) ppm.

$^1$H NMR (44 MHz) of R134 in Oleum34: 4.77 (2H, dq, J=45.1; 8.1 Hz, CH$_2$F)

The formation of FSO$_3$H was not detected after 16 h at 85° C. without utilization of an oxidant. Upon addition of an excess of K$_2$S$_2$O$_8$ the formation of FSO$_3$H can be detected and followed in the $^{19}$F NMR spectrum within 2 h. After 21 h at 85° C., 1,1,1,2 tetrafluorethane (R134) reacted quantitatively and the formation of FSO$_3$H in 85% yield was observed. The $^1$H NMR spectra indicate no formation of a major non-fluorinated byproduct, (e.g. such as methylene di(sulfate) or similar).

Example 6: Preparation of Fluoro Sulfonic Acid (FSO$_3$H) Via the Thermal Decomposition of 2,3,3,3,-Tetrafluorpropylen (R1234yf) in Fuming Sulfuric Acid

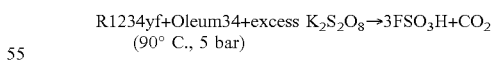
(90° C., 5 bar)

A high pressure NMR tube (NORELL, EXTREME Series Level 3, thin wall, Kalrez O-rings) was charged with 0.5 mL Oleum34 and subsequently pressurized with 5 bar 2,3,3,3,-tetrafluorpropylen (R1234yf). The reaction was followed by $^1$H and $^{19}$F NMR spectroscopy. $^{19}$F{$^1$H} (40.89 MHz) NMR of R1234yf in Oleum34: br s overlay with intrinsic residual peak of spectrometer at ca −74 (br) ppm.

The formation of FSO$_3$H was detected already after 15 min at ambient temperature without the addition of an oxidant. After 1 h at 90° C. the $^{19}$F NMR spectrum includes besides the singlet associated with FSO$_3$H at 44 ppm only three additional singlets (−70.0; −75.2; −76.4 ppm).

Remarkably, the absence of any J coupling indicates only C—F moieties without any coupling H or F neighboring atoms.

Pressure release did not result in the depletion of the singlet resonances associated with the initially formed byproducts, therefore we anticipate that the intermediates are not gaseous. To the mixture, an excess of $K_2S_2O_8$ was added (200 mg). Upon addition of $K_2S_2O_8$ vigorous gas formation was observed. The reaction mixture was further heated at 90° C. for 6 h in the closed NMR tube. An increase of the integral of the area peak associated with $FSO_3H$ was observed. However residual peaks remain in the area between −65 and −80 ppm.

Conversion: 100% of R1234yf

Yield: $FSO_3H$ 60% with respect to all F-containing products formed

Example 7 Preparation of Fluoro Sulfonic Acid ($FSO_3H$) Via the Thermal Decomposition of Perfluoro Octanoic Acid in Fuming Sulfuric Acid

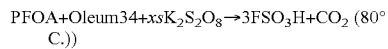

PFOA+Oleum34+$xsK_2S_2O_8$→3$FSO_3H$+$CO_2$ (80° C.))

A J Young NMR tube (NORELL) was charged with 0.5 mL Oleum34 and 15 mg perfluoro octanoic acid (PFOA) The reaction was followed by $^{19}F$ NMR spectroscopy. No reaction was observed in the absence of an oxidizer within 3 h at 80° C. Upon addition of an excess amount of $K_2S_2O_8$ and heating the sample at 80° C. for 30 min formation of $FSO_3H$ was observed by means of $^{19}F$ NMR spectroscopy. Allowing the mixture to react overnight (16 h) gave rise to a significant degradation of PFOA and concomitant formation of $FSO_3H$.

Conversion: 70% of PFOA

The invention claimed is:

1. A method for conversion of fluorinated carbons, comprising steps of reacting a fluorinated carbon with $SO_3$, wherein the method is performed in the absence of metal catalysts and the fluorinated carbon has a carbon number in the range of from 1 to 20; characterized in that the fluorinated carbon is reacted with sulfur trioxide to form fluorosulfonic acid.

2. The method according to claim 1, wherein the $SO_3$ is present as oleum.

3. The method according to claim 1, characterized in that the fluorinated carbon is a hydrocarbon in which at least one H-atom is replaced by fluorine, said hydrocarbon being selected from an alkane, an alkene, or an alkyne, wherein said hydrocarbon can be linear, branched or cyclic, substituted or un-substituted.

4. The method according to claim 1, characterized in that the molecular ratio between sulfur trioxide and fluorinated carbon is in the range of from 1 to 100.

5. The method according to claim 1, characterized in that the fluorinated carbon is reacted with sulfur trioxide at a temperature of 0 to 200° C.

6. The method according to claim 1, characterized in that the fluorinated carbon is reacted with sulfur trioxide at a pressure of 1 to 200 bar.

7. The method according to claim 1, characterized in that the fluorinated carbon comprises a single or multiple fluorine atoms, wherein one or more of the carbon atoms of the fluorinated carbon are bonded to one or more fluorinated atoms.

8. A method for conversion of fluorinated carbons, comprising steps of reacting a fluorinated carbon with $SO_3$, wherein the method is performed in the absence of metal catalysts and the fluorinated carbon has a carbon number in the range of from 1 to 20;
wherein the $SO_3$ is present as oleum;
wherein a peroxide compound is added to the reaction mixture comprising fluorinated carbon and oleum.

9. The method according to claim 8, wherein the peroxide is added stoichiometrically if the fluorinated carbon comprises more than 1 C-atom, and the peroxide is added sub-stoichiometrically if the fluorinated carbon comprises 1 C-atom.

10. The method according to claim 1, wherein one or more of methylene bis(fluorosulfate), fluoromethyl fluorosulfate, or methylene disulfate occur during the reaction.

11. The method according to claim 10, wherein the one or more of methylene bis(fluorosulfate) or fluoromethyl fluorosulfate is separated from the reaction mixture.

12. The method of claim 1, further comprising recycling or disposing of a reaction product of the conversion of fluorinated carbons.

13. The method of claim 12, characterized in that the fluorinated carbon is a fluoroalkane.

14. The method according to claim 5, characterized in that the fluorinated carbon is reacted with sulfur trioxide at a pressure of 1 to 200 bar.

15. The method according to claim 8, characterized in that the fluorinated carbon is reacted with sulfur trioxide to form fluorosulfonic acid.

16. The method according to claim 5, characterized in that the fluorinated carbon is reacted with sulfur trioxide at a temperature of 80° C. to 125° C.

17. A method for conversion of fluorinated carbons, comprising steps of reacting a fluorinated carbon with $SO_3$, wherein the method is performed in the absence of metal catalysts and the fluorinated carbon has a carbon number in the range of from 1 to 20; wherein the fluorinated carbon is a $CF_3H$.

18. The method according to claim 17, characterized in that the molecular ratio between sulfur trioxide and fluorinated carbon is in the range of from 1 to 100.

19. The method according to claim 17, characterized in that the fluorinated carbon is reacted with sulfur trioxide at a temperature of 0 to 200° C.

20. The method according to claim 17, characterized in that the fluorinated carbon is reacted with sulfur trioxide at a pressure of 1 to 200 bar.

* * * * *